(12) United States Patent
Robinson et al.

(10) Patent No.: US 8,469,936 B2
(45) Date of Patent: Jun. 25, 2013

(54) REDUCED-PRESSURE DRESSINGS, SYSTEMS, AND METHODS EMPLOYING DESOLIDIFYING BARRIER LAYERS

(75) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 228 days.

(21) Appl. No.: 12/823,958

(22) Filed: Jun. 25, 2010

(65) Prior Publication Data

US 2011/0015595 A1 Jan. 20, 2011

Related U.S. Application Data

(60) Provisional application No. 61/225,604, filed on Jul. 15, 2009.

(51) Int. Cl.
| | |
|---|---|
| *A61M 1/00* | (2006.01) |
| *A61M 37/00* | (2006.01) |
| *A61M 35/00* | (2006.01) |
| *A61M 25/16* | (2006.01) |
| *A61M 27/00* | (2006.01) |
| *A61F 13/00* | (2006.01) |
| *A61F 15/00* | (2006.01) |
| *A61L 15/16* | (2006.01) |

(52) U.S. Cl.
USPC ............ 604/319; 604/46; 604/289; 604/305; 604/313; 604/534; 604/543; 602/41; 602/43; 602/53; 602/48; 424/446

(58) Field of Classification Search
USPC .................. 604/319, 46, 534, 313, 289, 543, 604/305; 424/446; 602/41, 43, 53, 48
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Jacqueline Stephens
*Assistant Examiner* — Andrew J Mensh

(57) ABSTRACT

Reduced-pressure medical dressings, systems, and methods involve a dressing with a first barrier layer that desolidifies when exposed to a fluid—typically a liquid—to form a treatment aperture in the first barrier that is used to deliver reduced pressure to a tissue site. The first barrier layer is formed from a desolidifying material. The system includes a drape covering a second surface of a manifold and a portion of the patient's epidermis to provide a substantially sealed space containing a manifold and the first barrier layer. Other systems, dressings, and methods are also disclosed.

20 Claims, 3 Drawing Sheets

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,503,527 B1 | 1/2003 | Whitmore et al. |
| 6,515,075 B1 | 2/2003 | Balogh et al. |
| 6,553,998 B2 | 4/2003 | Heaton et al. |
| 6,814,079 B2 | 11/2004 | Heaton et al. |
| 7,105,629 B2 | 9/2006 | Matsuda et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0073151 A1* | 4/2004 | Weston ............ 602/41 |
| 2006/0293630 A1 | 12/2006 | Manna et al. |
| 2007/0185426 A1 | 8/2007 | Ambrosio et al. |
| 2007/0237812 A1 | 10/2007 | Patel et al. |
| 2008/0125687 A1* | 5/2008 | Flick et al. ......... 602/48 |
| 2008/0132602 A1 | 6/2008 | Rizk et al. |
| 2009/0198167 A1* | 8/2009 | Ambrosio ........... 602/46 |
| 2010/0069863 A1* | 3/2010 | Olson ............. 604/368 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/008032 A1 | 1/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstertrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of the Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method of Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax,"*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Metods of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

International Search Report and Written Opinion date mailed Dec. 30, 2010 for PCT/US2010/040218.

www.KurarayAmericaPVOH-PVB-MowiflexPVOHProduct.htm "Thermoplastic Processing of Mowiol/PVOH" Sep. 2004.

* cited by examiner

REDUCED-PRESSURE DRESSINGS, SYSTEMS, AND METHODS EMPLOYING DESOLIDIFYING BARRIER LAYERS

RELATED APPLICATION

The present invention claims the benefit, under 35 USC §119(e), of the filing of U.S. Provisional Patent Application Ser. No. 61/225,604 entitled "Reduced-Pressure Dressings, Systems, and Methods Employing Desolidifying Barrier Layers," filed Jul. 15, 2009, which is incorporated herein by reference for all purposes.

BACKGROUND

The disclosure relates generally to medical treatment systems, and more particularly, but not by way of limitation, to reduced-pressure dressings, systems, and methods employing desolidifying barrier layers.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity.

SUMMARY

Improvements to existing reduced-pressure treatment apparatuses, systems, and methods may be realized by the apparatuses, systems, and methods of the illustrative, non-limiting embodiments herein. According to an illustrative, non-limiting embodiment, a system for providing reduced-pressure therapy to a tissue site of a patient includes a reduced-pressure source for supplying reduced pressure and a manifold having a first, inward-facing surface and a second surface. The manifold is operable to transfer the reduced pressure. The system includes a first barrier layer covering at least a portion of the first, inward-facing surface of the manifold. The first barrier layer is for placement adjacent the tissue site and the first barrier layer is formed from a desolidifying material. The system also includes a drape for covering the second surface of the manifold and a portion of the patient's epidermis to provide a substantially sealed space containing the manifold and the first barrier layer.

According to another illustrative, non-limiting embodiment, an apparatus includes a manifold having a first, inward-facing surface and a second surface. The manifold is operable to transfer reduced pressure. The apparatus also includes a first barrier layer covering at least a portion of the first, inward-facing surface of the manifold. The first barrier layer is formed from a desolidifying material.

According to another illustrative, non-limiting embodiment, a method for providing reduced-pressure therapy to a tissue site of a patient includes applying a dressing to the tissue site. The dressing includes a manifold having a first, inward-facing surface and a second surface, and the manifold is operable to transfer reduced pressure. The dressing also includes a first barrier layer covering at least a portion of the first, inward-facing surface of the manifold. The first barrier layer is formed from a desolidifying material. The method also includes allowing fluid at the tissue site to desolidify at least a portion of the first barrier layer to create a treatment aperture and applying a reduced pressure to the tissue site via the treatment aperture.

According to another illustrative, non-limiting embodiment, a method of manufacturing an apparatus for providing reduced-pressure therapy to a tissue site of a patient includes providing a manifold having a first, inward-facing surface and a second surface, and providing a first barrier layer formed from a desolidifying material. The method also includes coupling the first barrier layer to the first, inward-facing surface of the manifold.

DETAILED DESCRIPTION

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1A:
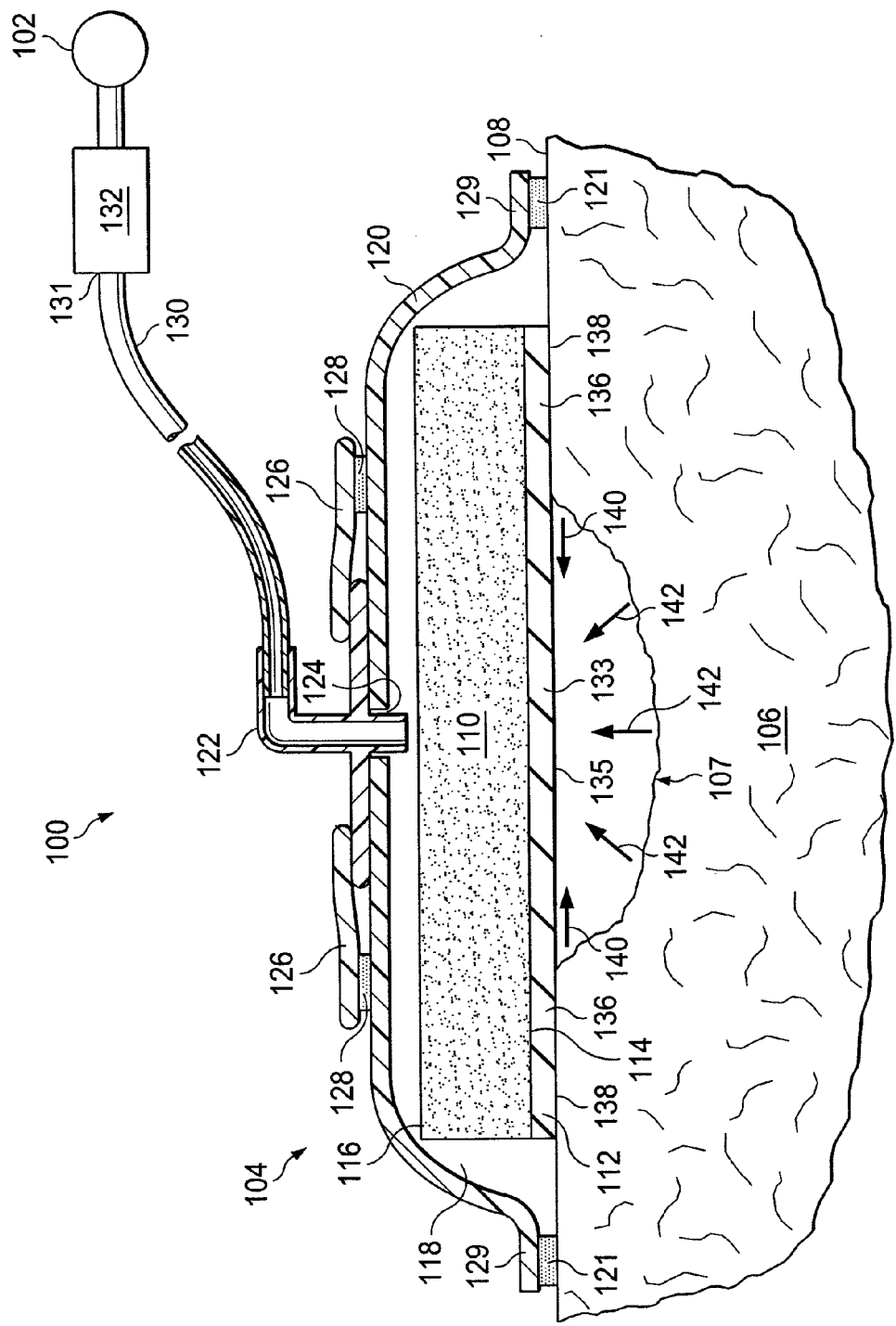
FIG. 1A is a schematic, cross-sectional view, with a portion shown as a block diagram, of a reduced-pressure treatment system according to one illustrative, non-limiting embodiment.
Figure 1B:
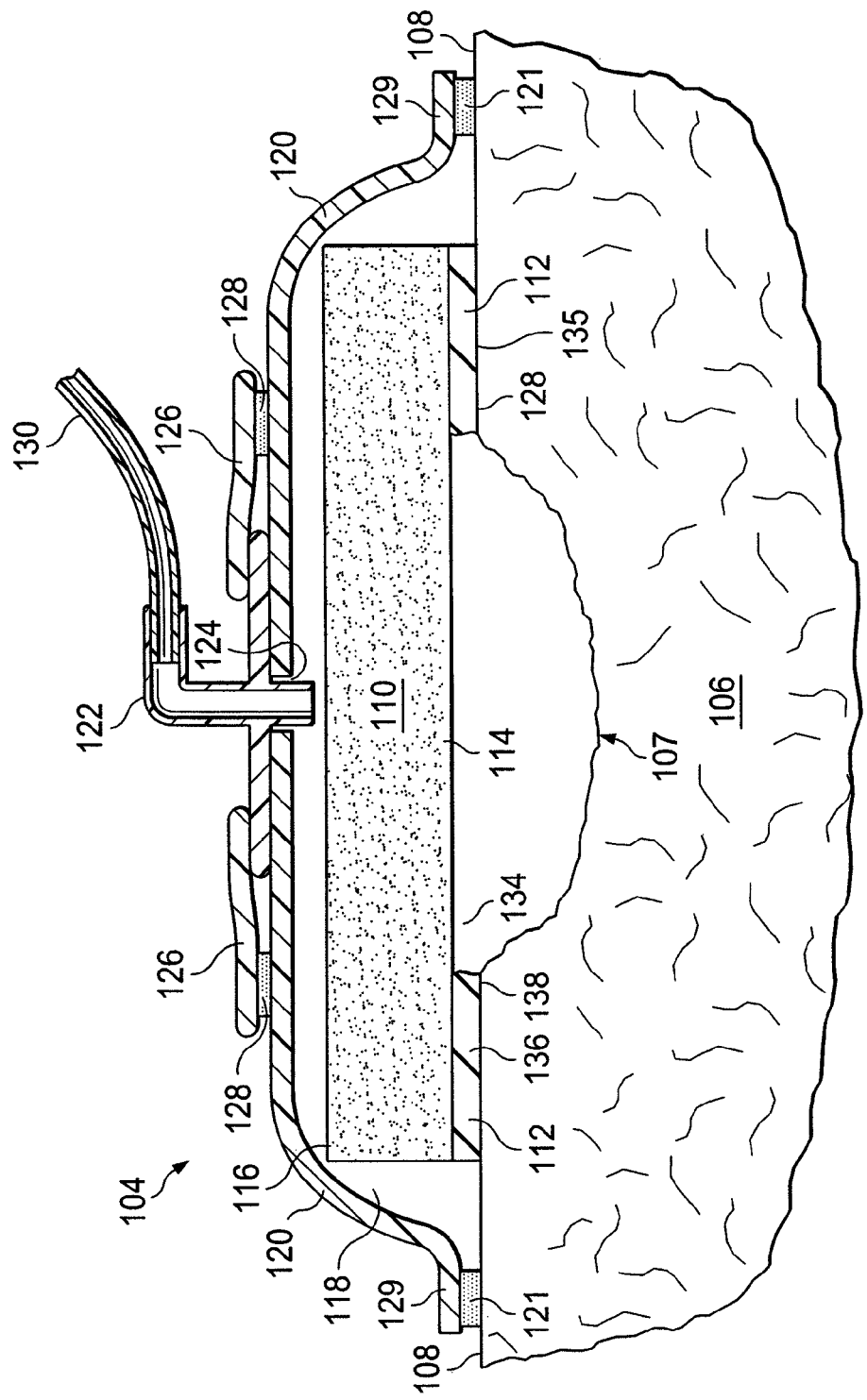
FIG. 1B is a schematic, cross-sectional view of the dressing shown in FIG. 1A in which a portion of the first barrier layer has desolidified.
Figure 1C:
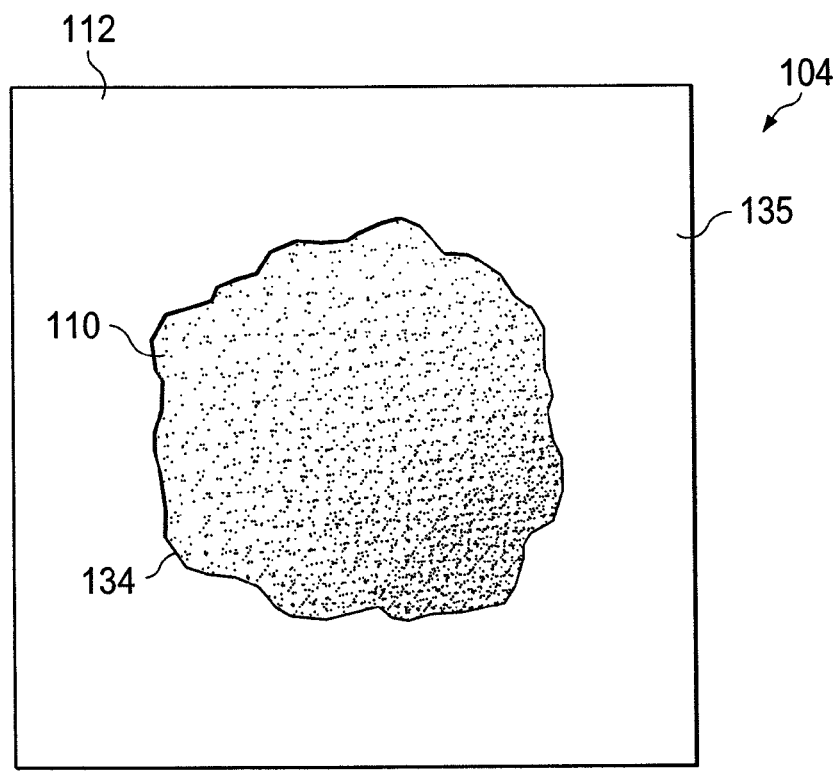
FIG. 1C is a schematic, plan view of the dressing shown in FIG. 1B from the perspective of the tissue site.

Referring now to the drawings and primarily to FIGS. 1A through 1C, a reduced-pressure therapy system 100, which includes a reduced-pressure source 102 and a dressing 104, is shown according to an illustrative, non-limiting embodiment. The dressing 104 includes a manifold 110 and a first barrier layer 112 that is configured to help avoid maceration of intact skin and to encourage epithelialization. The dressing 104 is applied to a tissue site 106, which may include a wound 107, of a patient 108 so that reduced pressure from the reduced-pressure source 102 can be transferred to the tissue site 106 via the dressing 104.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 106 may include removal of fluids, e.g., ascites, exudate, or delivery of reduced pressure. The wound 107 on the tissue site 106 may be due to a variety of causes, including trauma or surgery.

The dressing 104 includes the manifold 110 and the first barrier layer 112. The manifold 110 includes a first, inward-facing (tissue-facing) surface 114 and a second surface 116. The term "manifold" as used herein generally refers to a substance or structure that is provided to assist in applying reduced pressure to, delivering fluids to, or removing fluids from a tissue site 106. The manifold 110 typically includes a plurality of flow channels or pathways that improve distribution of fluids provided to and removed from the tissue site 106 around the manifold 110. The plurality of flow channels may be interconnected. The manifold 110 may be a biocompatible material that is capable of being placed in contact with the tissue site 106 and distributing reduced pressure to the tissue site 106. Examples of the manifold 110 may include, for example, without limitation, devices that have structural elements arranged to form flow channels, such as, for example, cellular foam, open-cell foam, porous tissue collections, liquids, gels, and foams that include, or cure to include, flow channels. The manifold 110 may be porous and may be made from foam, gauze, felted mat, or any other material suited to a particular biological application. In one embodiment, the manifold 110 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments may include "closed cells." In some situations, the manifold 110 may also be used to distribute fluids, such as medications, antibacterials, growth factors, and various solutions to the tissue site 106. Other layers may be included in or on the manifold 110, such as absorptive materials, wicking materials, hydrophobic materials, and hydrophilic materials.

The dressing 104 also includes the first barrier layer 112 that covers at least a portion of the first, inward-facing surface 114 of the manifold 110. The first barrier layer 112 is disposed adjacent to the tissue site 106 such that the first barrier layer 112 is disposed between the manifold 110 and the tissue site 106. The first barrier layer 112 may be fixedly or non-fixedly attached to the manifold 110. For example, the first barrier layer 112 may simply abut the manifold 110 without the aid of an adhesive or another attachment device. Also, the first barrier layer 112 may be coupled to the manifold 110. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Specific non-limiting examples of the techniques by which the first barrier layer 112 may be coupled to the manifold 110 include welding (e.g., ultrasonic or RF welding), bonding, adhesives, cements, or other coupling techniques or devices.

The manifold 110 and the first barrier layer 112 are disposed within a sealed space 118 that is formed by a drape 120 that covers both the manifold 110 and the first barrier layer 112. The sealed space 118 that is formed by the drape 120 helps to maintain a therapeutic reduced pressure at the tissue site 106 and may include various components, such as the manifold 110 and the first barrier layer 112.

The drape 120 may be any material that provides a fluid seal. The drape 120 may, for example, be an impermeable or semi-permeable, elastomeric material. "Elastomeric" means having the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of the drape 120 include a silicone drape, 3M Tegaderm® drape, or a polyurethane drape such as one available from Avery Dennison of Pasadena, Calif.

An adhesive 121 may be used to hold the drape 120 against a patient's epidermis 138 or another layer, such as a gasket or additional drape. The adhesive 121 may take numerous forms. For example, the adhesive 121 may be a medically acceptable, pressure-sensitive adhesive that extends about a periphery 129 of the drape 120.

Reduced pressure is delivered to the sealed space 118 via a reduced-pressure interface or a connector 122. The connector 122 is at least partially disposed in an aperture 124 of the drape 120. The connector 122 may be held against the drape 120 using a second drape 126 that is held against the drape 120 using an adhesive 128. The adhesive 128 may be the same or similar to the adhesive 121 that is used to hold the drape 120 against the patient's epidermis 138. The second drape 126 can also be held against the connector 122 using an adhesive (not shown). In one illustrative embodiment, the connector 122 is a T.R.A.C.® Pad or Sensa T.R.A.C.® Pad available from KCI of San Antonio, Tex.

A reduced-pressure conduit 130 is used to deliver reduced pressure from the reduced-pressure source 102 to the connector 122. The reduced-pressure conduit 130 may include one or a plurality of lumens, each of which is capable of transferring reduced pressure or fluid. A medial portion 131 of the reduced-pressure conduit 130 may have one or more devices, such as a representative device 132. For example, the device 132 may be a fluid reservoir, or collection member, to hold exudates and other fluids removed from the tissue site 106. Other examples of the device 132 that may be included on the medial portion 131 of the reduced-pressure conduit 130, or otherwise fluidly coupled to the reduced-pressure conduit 130, include the following non-limiting examples: a pressure-feedback device, a volume detection system, a blood detection system, an infection detection system, a flow monitoring system, or a temperature monitoring system. Some of these devices may be formed integrally to the reduced-pressure source 102. For example, a reduced-pressure port on reduced-pressure source 102 may include a filter member that includes one or more filters, e.g., an odor filter. Multiple devices 132 may be included.

The reduced-pressure source 102 may be any device for supplying a reduced pressure, such as a vacuum pump, wall suction, or other source. While the amount and nature of reduced pressure applied to the tissue site 106 will typically vary according to the application, the reduced pressure will typically be between −5 mm Hg and −500 mm Hg and more typically between −100 mm Hg and −300 mm Hg.

The first barrier layer 112 is formed from a desolidifying material. "Desolidifying material" means a material operable to desolidify in the presence of fluid, such as a liquid. Desolidification allows fluid communication to occur where the desolidifying material has desolidified. Desolidification in this context includes dissolving, degrading, breaking apart, increasing fluid permeability, or transitioning from a solid to a liquid or other state, including a gel or gas. In some embodiments, the desolidifying material is removed or dissolved in the presence of liquid and in other embodiments the desolidifying material remains in part but allows fluid communication.

The first barrier layer 112 may be a flexible layer capable of conforming to the contours of the tissue site 106 and desolidifying in the presence of a fluid—typically a liquid. Non-limiting examples of materials from which the first barrier layer 112 may be formed include straight-chain polymers and a variety of water-soluble films, such as polyvinyl alcohol, polyethylene oxide, cellulose derivatives, such as the sodium salt of carboxy methyl cellulose, polyvinyl pyrrolidone, or acrylics, such as polyacrylic acid, salts of polyacrylic acid, hydroxyl and carboxyl substituted polymers, and copolymers of acrylics and polyurethanes and their salts. The first barrier layer 112 may also be formed using a bioabsorbable material that relies on biological absorption to desolidify the first barrier layer 112. Such bioabsorbable materials may desolidify in the presence of biological material present at the tissue site 106, including particular biological groups that promote healing in the wound 107.

According to another illustrative, non-limiting embodiment, in operation, the dressing 104 is applied to the tissue site 106 of the patient 108 such that the first barrier layer 112 is adjacent or abutting the tissue site 106 and may be adjacent to a portion of the patient's intact epidermis 138 as shown in FIG. 1A. When the dressing 104 is applied to the tissue site 106 of the patient 108, the first barrier layer 112 may be brought into the presence of or into contact with a fluid, including a liquid. The source of this fluid is described in further detail below. The fluid desolidifies a first portion 133 of the first barrier layer 112 to form a treatment aperture 134 in the first barrier layer 112 as shown in FIGS. 1B and 1C. The first barrier layer 112 may desolidify, at least partially, by dissolving when exposed to the fluid. The treatment aperture 134 exposes the manifold 110 to the tissue site 106 such that fluid communication is provided between the manifold 110 and the tissue site 106. In this way, reduced pressure from the reduced-pressure source 102 may be applied to the tissue site 106 through the treatment aperture 134.

A second portion 136, or intact portion, of the first barrier layer 112 remains intact and does not desolidify when the reduced pressure is applied to the tissue site 106. The second portion 136 separates the manifold 110 from the epidermis 138 of the patient 108 and can prevent or reduce irritation of the patient's epidermis 138 caused by the manifold 110. The first barrier layer 112 can have a smooth inward-facing surface 135 that facilitates the inward migration of healthy skin toward the wound 107 in the direction of arrow 140. Thus, the first barrier layer 112 encourages epithelialization of the wound 107. Also, the first barrier layer 112 may have a moisture-vapor transmission rate (MVTR) that helps to prevent maceration of the portion of the patient's epidermis 138 that touches the second portion 136 of the first barrier layer 112. Using the illustrative embodiments, the dressing 104, and in particular the manifold 110 and the first barrier layer 112, need not be cut to fit the wound 107 because these components may overlay tissue surrounding the wound 107, such as the patient's epidermis 138, without unwanted maceration or irritation.

The fluid that causes the desolidification of at least a portion of the first barrier layer 112 may come from any of a variety of sources. For example, when reduced pressure is applied to the wound 107, exudate from the wound 107 may be drawn toward the first barrier layer 112 as indicated by the arrows 142. The exudate may then desolidify the first portion 133 of the first barrier layer 112 with which the exudate comes into contact to create the treatment aperture 134. In another, illustrative, non-limiting embodiment, a gel (not shown) may be applied to the tissue site 106 or the wound 107 prior to applying the dressing 104 to the tissue site 106. The gel, which may be a water-based gel, may then act to desolidify the first portion 133 of the first barrier layer 112 with which the gel comes into contact. In yet another illustrative, non-limiting example, fluid may be provided to the dressing 104, and in particular the first barrier layer 112, by a fluid source (not shown) that supplies fluid through the reduced-pressure conduit 130. In one embodiment, the device 132 may act as the fluid source.

The dressing 104 may be used on both dry and wet tissue sites. In the example in which the first barrier layer 112 is used on a relatively dry tissue site, the first barrier layer 112 may be formed from a material that desolidifies in the presence of a lower amount of fluid. Alternatively, a gel, including a water-based gel, or colloid may be applied to the relatively dry tissue site before applying the dressing 104, and this pre-applied gel will cause the first barrier layer 112 to desolidify. In the contrasting case in which the tissue site 106 is relatively moist, the first barrier layer 112 may be formed from a material that desolidifies in response to larger amounts of fluid.

In another illustrative, non-limiting embodiment, the first barrier layer 112, when brought into the presence of a fluid, may first turn into a gel before desolidifying into a liquid. The gel formed during the transition period between the solid and liquidified first barrier layer 112 may contain healing agents that are released into the wound 107. Examples of the healing agents that may be released from this gel include ionic groups, antimicrobials, anti-inflammatory factors, and growth factors. Other healing factors that are beneficial to the condition of the wound 107 or epidermis 138 and that encourage epithelialization may also be included in the gel. When the first barrier layer 112 desolidifies into a liquid, the liquid may be drawn through the manifold 110 and out of the dressing 104 using the reduced pressure that is supplied by the reduced-pressure source 102.

In other illustrative, non-limiting embodiments, additional layers may be added to the sealed space 118. For example, an absorbent layer, another manifold layer, another barrier layer, or other layers or components that facilitate reduced-pressure therapy may be included in the dressing 104 and disposed in the sealed space 118.

Figure 2:
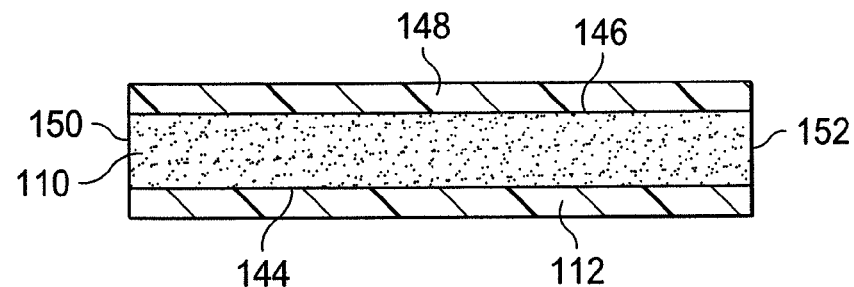
FIG. 2 is a schematic, cross-sectional view of a manifold and a first and second barrier layer shown according to an illustrative, non-limiting embodiment.

Referring now primarily to FIG. 2, another illustrative, non-limiting embodiment, the manifold 110 includes two surfaces 144 and 146 covered by the first barrier layer 112 and a second barrier layer 148, respectively. The first barrier layer 112 and the second barrier layer 148 may be formed from the same or different materials. In the example in which the first and second barrier layers 112, 148 are formed from a same or similar material, a caregiver may pay little or no regard to whether the first barrier layer 112 or the second barrier layer 148 is deployed adjacent to the tissue site, e.g., the tissue site 106 in FIG. 1. In the example in which the first and second barrier layers 112, 148 are different, however, a caregiver may choose between placing either the first or second barrier layers 112, 148 against the tissue site 106 based on the properties of each barrier layer 112, 148. The first and second barrier layers 112, 148 may each have different properties that are adapted for treating different types of wounds or conditions. For example, the first barrier layer 112 may be formed from a material that requires less fluid to desolidify than the second barrier layer 148. In this example, the first barrier layer 112 may be used for relatively drier wounds than the wounds for which the second barrier layer 148 is used.

The first and second barrier layers 112, 148 may also differ in other respects. For example, the first and second barrier layers 112, 148 may each respectively contain different healing agents that are adapted for different tissues or wound types. The first and second barrier layers 112, 148 may also each have a different moisture vapor transmission rates, hardness, smoothness, thickness, or other properties. In another illustrative, non-limiting example, either or both of the first and second barrier layers 112, 148 may be partially or wholly formed from a debridement material that encourages debridement at the tissue site through autolytic mechanisms. Either or both of the first and second barrier layers 112, 148 may also be able to release debridement agents (e.g., enzymes) that break down tissue, such as eschar and necrotic tissue. In another illustrative, non-limiting embodiment, each lateral side 150, 152 of the manifold 110 may also be covered by a barrier layer.

Figure 3:
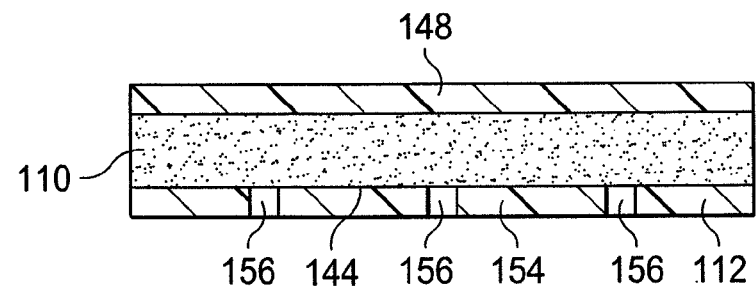
FIG. 3 is a schematic, cross-sectional view of a manifold according to an illustrative, non-limiting embodiment, which has a first and second barrier layer in which one of the barrier layers has a plurality of perforations.

Referring now primarily to FIG. 3, a first barrier layer 154 having perforations 156 covers a first surface 144 of a manifold 110. The perforations 156 in the first barrier layer 154 provide immediate fluid communication between the manifold 110 and a tissue site when the dressing associated therewith is applied to the tissue site. Thus, reduced pressure may be applied to the tissue site, via the perforations 156, before the first barrier layer 154 desolidifies. The perforations 156 may be uniform or non-uniform in size and may take any shape. The perforations 156 may be engulfed, or simply disappear, when the first barrier layer 154 desolidifies.

In another illustrative, non-limiting embodiment, the second barrier layer 148 may also include a plurality of perforations (not shown). In this embodiment, the percentage of the total surface area of each of the first and second barrier layers 154, 148 that is occupied by the perforations in each of these barrier layers 154, 148 may differ. For example, the first barrier layer 154 may have a higher density of perforations 156 than the second barrier layer 148. The perforations 156 in the first barrier layer 154 may also be larger or smaller than the perforations in the second barrier layer 148.

The perforations in each of the first and second barrier layers 154, 148 may also provide different fluid flow rates for each of these barrier layers before or during the time at which they desolidify. In this example, the perforations 156 in the first barrier layer 154 provide a flow rate X across the first barrier layer 154 for a given fluid and reduced pressure, while the perforations in the second barrier layer 148 provide a flow rate Y across the second barrier layer 148 for the same fluid and reduced pressure. The flow rate Y may be the same as or greater than X. By differing the flow rates between the first and second barrier layers 154, 148, each of these barrier layers may be used for particular types of wounds. In the example in which the second barrier layer 148 has a flow rate Y greater than the flow rate X in the first barrier layer 154, the second barrier layer 148 may be suited for placement adjacent to wounds that are drier wounds. These aforementioned embodiments that include differing barrier layers on different sides of the manifold 110 allow a caregiver to provide two treatment scenarios with a single dressing.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

We claim:

1. A system for providing reduced-pressure therapy to a tissue site of a patient, the system comprising:
    a reduced-pressure source for supplying reduced pressure;
    a manifold having a first, inward-facing surface and a second surface, the manifold operable to transfer the reduced pressure;
    a first barrier layer covering at least a portion of the first, inward-facing surface of the manifold, the first barrier layer comprising a first portion and a second portion formed from a desolidifying material; and
    a drape for covering the second surface of the manifold and a portion of the patient's epidermis to provide a substantially sealed space containing the manifold and the first barrier layer;
    wherein the first portion is adapted to desolidify and form a treatment aperature under reduced pressure, while the second portion is adapted to separate the manifold from epidermis adjacent to the tissue site and remain intact under reduced pressure.

2. The system of claim 1, further comprising:
    a second barrier layer covering the second surface of the manifold, the second barrier layer operable to desolidify in the presence of fluid to expose the manifold.

3. The system of claim 1, further comprising:
    a second barrier layer covering the second surface of the manifold, the second barrier layer operable to desolidify in the presence of fluid to expose the manifold to the tissue site, wherein the second barrier layer desolidifies at a faster rate than the first barrier layer when in the presence of the fluid.

4. The system of claim 1, wherein the first barrier layer is formed with a plurality of perforations for providing fluid communication across the first barrier layer.

5. The system of claim 1, wherein the first barrier layer comprises a first plurality of perforations for providing fluid communication across the first barrier layer, and further comprising:
    a second barrier layer on the second surface of the manifold, the second barrier layer comprising a second plurality of perforations for providing fluid communication across the second barrier layer.

6. The system of claim 1, wherein the first barrier layer comprises a first plurality of perforations for providing a flow rate (X) across the first barrier layer, and further comprising:
    a second barrier layer on the second surface of the manifold, the second barrier layer comprising a second plurality of perforations for providing a flow rate (Y) across the second barrier layer, wherein Y is greater than X.

7. The system of claim 1, wherein the first portion of the first barrier layer is operable to desolidify into a liquid when contacting a fluid.

8. The system of claim 1, wherein the desolidifying material becomes substantially fluid permeable in the presence of a liquid.

9. An apparatus for providing reduced-pressure therapy to a tissue site of a patient, the apparatus comprising:
- a manifold having a first, inward-facing surface and a second surface, the manifold operable to transfer reduced pressure; and
- a first barrier layer covering at least a portion of the first, inward-facing surface of the manifold, the first barrier layer comprising a first portion and a second portion formed from a desolidifying material;
- wherein the first portion is adapted to desolidify and form a treatment aperature under reduced pressure, while the second portion is adapted to separate the manifold from epidermis adjacent to the tissue site and remain intact under reduced pressure.

10. The apparatus of claim 9, further comprising:
- a second barrier layer covering the second surface of the manifold, the second barrier layer operable to desolidify in the presence of a fluid to expose the manifold to the tissue site.

11. The apparatus of claim 9, further comprising:
- a second barrier layer covering the second surface of the manifold, the second barrier layer operable to desolidify in the presence of a fluid to expose the manifold to the tissue site, and wherein the second barrier layer desolidifies at a faster rate than the first barrier layer when in the presence of the fluid.

12. The apparatus of claim 9, wherein the first barrier layer comprises a plurality of perforations providing fluid communication across the first barrier layer.

13. The apparatus of claim 9, wherein the first barrier layer comprises a first plurality, of perforations for providing fluid communication across the first barrier layer, and further comprising:
- a second barrier layer on the second surface of the manifold, the second barrier layer comprising a second plurality of perforations for providing fluid communication across the second barrier layer.

14. The apparatus of claim 9, wherein the first barrier layer comprises a first plurality of perforations for providing a flow rate (X) across the first barrier layer, and further comprising:
- a second barrier layer on the second surface of the manifold, the second barrier layer comprising a second plurality of perforations for providing a flow rate (Y) across the second barrier layer, wherein Y is greater than X.

15. The apparatus of claim 9, wherein the first barrier layer is operable to desolidify into a liquid when contacting the fluid.

16. The apparatus of claim 9, wherein the first barrier layer includes a healing agent, and wherein the healing agent is released as the first barrier layer desolidifies.

17. A method for providing reduced-pressure therapy to a tissue site of a patient, the method comprising:
- applying a first portion and a second portion of a barrier layer over the tissue site, wherein the second portion is applied to epidermis adjacent to the tissue site;
- applying a manifold over the barrier layer such that the second portion of the barrier layer is disposed between the manifold and the epidermis;
- desolidifying the first portion to create a treatment aperture while the second portion remains intact; and
- applying a reduced pressure to the tissue site via the treatment aperture.

18. The method of claim 17, wherein applying the reduced pressure to the tissue site includes drawing a desolidified portion of the barrier layer material out of the dressing via the manifold.

19. The method of claim 17, further comprising:
- applying a fluid to the dressing from a fluid source to facilitate the desolidification of the barrier layer.

20. The method of claim 17, further comprising covering the manifold and the barrier layer with a drape to provide a substantially sealed space containing the manifold and the barrier layer.

* * * * *